US007830249B2

(12) United States Patent
Dorneich et al.

(10) Patent No.: US 7,830,249 B2
(45) Date of Patent: Nov. 9, 2010

(54) COMMUNICATIONS SYSTEM BASED ON REAL-TIME NEUROPHYSIOLOGICAL CHARACTERIZATION

(75) Inventors: Michael C. Dorneich, St. Paul, MN (US); Stephen D. Whitlow, St. Louis Park, MN (US); Patricia M. Ververs, Ellicott City, MD (US); James C. Carciofini, Centerville, MN (US); Janet Creaser, St. Anthony, MN (US)

(73) Assignee: Honeywell International Inc., Morristown, NJ (US)

( * ) Notice: Subject to any disclaimer, the term of this patent is extended or adjusted under 35 U.S.C. 154(b) by 1529 days.

(21) Appl. No.: 11/148,537

(22) Filed: Jun. 9, 2005

(65) Prior Publication Data

US 2006/0029198 A1  Feb. 9, 2006

Related U.S. Application Data

(60) Provisional application No. 60/578,812, filed on Jun. 9, 2004.

(51) Int. Cl.
*G08B 1/08* (2006.01)
(52) U.S. Cl. .................. 340/539.12; 379/38; 455/552.1
(58) Field of Classification Search .............. 340/573.1, 340/539.12; 455/41, 552.1; 379/38
See application file for complete search history.

(56) References Cited

U.S. PATENT DOCUMENTS

| 4,487,583 | A | * | 12/1984 | Brucker et al. ................. 434/22 |
| 4,948,371 | A | * | 8/1990 | Hall ............................ 434/21 |
| 5,295,491 | A | | 3/1994 | Gevins |
| 5,377,100 | A | | 12/1994 | Pope et al. |
| 5,406,957 | A | | 4/1995 | Tansey |
| 5,447,166 | A | | 9/1995 | Gevins |
| 5,571,057 | A | | 11/1996 | Ayers |
| 5,740,812 | A | | 4/1998 | Cowan |

(Continued)

FOREIGN PATENT DOCUMENTS

EP  0846440  6/1998

OTHER PUBLICATIONS

Eaton, "Part One: 3D Audio Relieves Military Information Overload," *COTS Journal*, 42-46, Mar. 2002.

(Continued)

*Primary Examiner*—Curtis Kuntz
*Assistant Examiner*—Maria El-Zoobi
(74) *Attorney, Agent, or Firm*—Ingrassia Fisher & Lorenz, P.C.

(57) ABSTRACT

A communications system is provided that includes a communications scheduler adapted to receive messages from a plurality of message sources and sensors. The messages comprise human and generated messages. The sensors comprise situational, neurophysiological and physiological sensors. The cognitive state profile processing unit receives sensor data and produces a current cognitive state profile for the user. The communications scheduler includes a context manager that receives outputs from the plurality of sensors, monitors a current user's tasks, and retains information about the user's environment, a message characterization unit that characterizes the messages using the attributes of the message, outputs from the sensors, and the user's specific baseline profile data and a presentation unit that receives the characterized messages, the cognitive state profile, and context information and queues the characterized messages into a prioritized message list and presents the message list to the user via the display unit.

36 Claims, 4 Drawing Sheets

U.S. PATENT DOCUMENTS

Figure 1A:
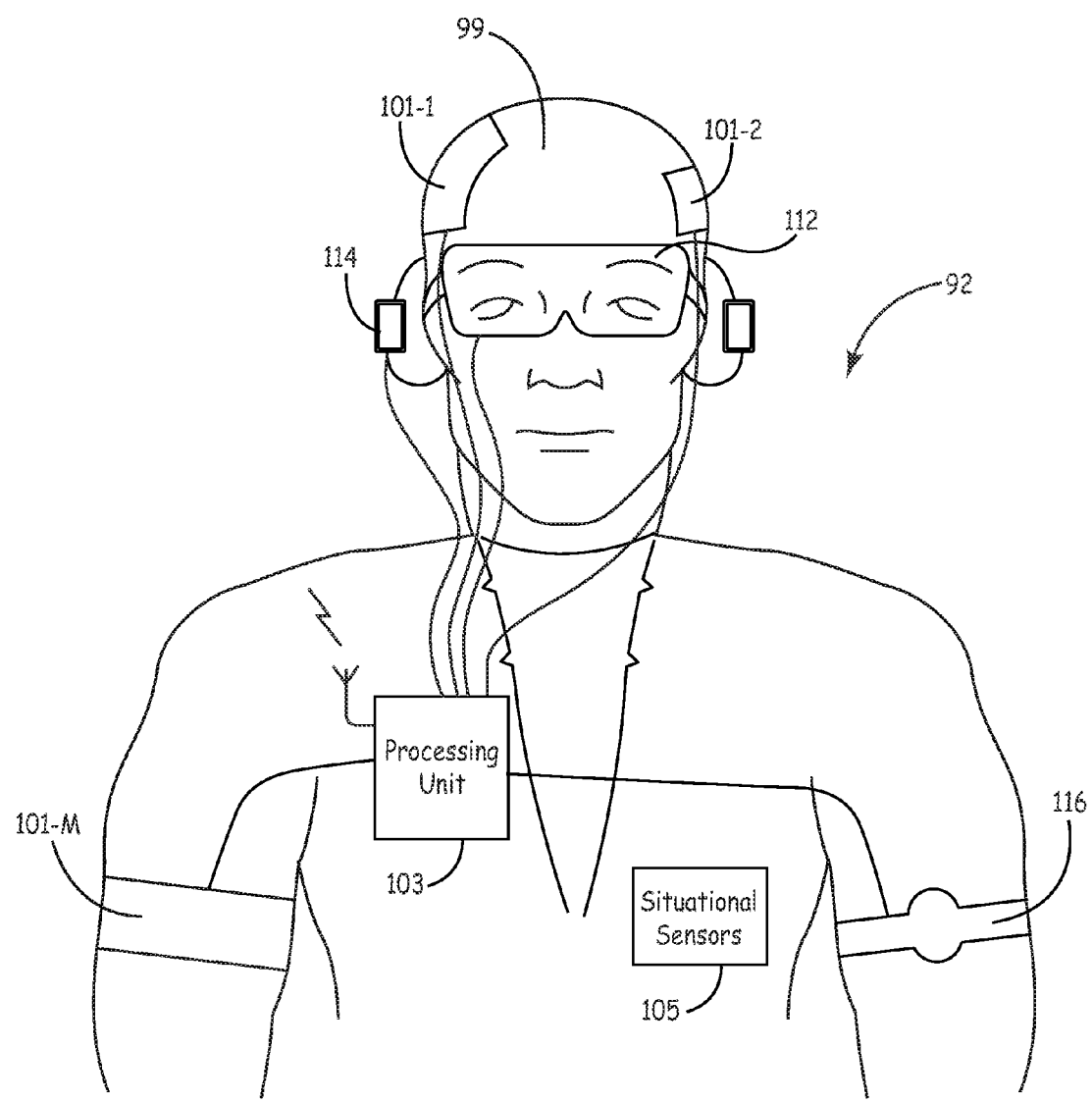

| | | | | |
|---|---|---|---|---|
| 5,771,001 | A * | 6/1998 | Cobb | 340/573.1 |
| 6,097,981 | A | 8/2000 | Freer | |
| 6,434,419 | B1 | 8/2002 | Gevins et al. | |
| 7,244,231 | B2 * | 7/2007 | Dewing et al. | 705/2 |
| 2002/0183006 | A1 * | 12/2002 | Yasushi et al. | 455/41 |
| 2003/0027103 | A1 * | 2/2003 | Preston et al. | 434/11 |
| 2003/0135128 | A1 * | 7/2003 | Suffin et al. | 600/544 |
| 2003/0214408 | A1 * | 11/2003 | Grajales et al. | 340/573.1 |
| 2004/0033472 | A1 * | 2/2004 | Varshneya | 434/23 |
| 2007/0111753 | A1 * | 5/2007 | Vock et al. | 455/552.1 |

OTHER PUBLICATIONS

Affective Computing: Sensing Human Affect, "Research on Sensing Human Affect," 6 pp., http://affect.media.mit.edu/AC_research/sensing.html, downloaded on Jun. 4, 2004.

Nature Interface, No. 14, 5 pp., http://www.natureinterface.com/e/ni14/P026-033/, downloaded on Jun. 4, 2004.

Primate Physiological Sensors, 2 pp., http://lifescie.arc.nasa.gov/lis/Hardware_App/primate6.html, downloaded on Jun. 4, 2004.

The National Academies, "US Army Medical Research and Material Command (AMRMC) US Army Research Institute of Environmental Medicine," 1 p., http://www4.nas.edu/pga/rap.nsf/0/540DFEA964167E0085256DC10069EEC4..., downloaded on Jun. 4, 2004.

Healy, "The Physiological Sensors," 2 pp., http//vismod.media.mit.edu/tech-reports/TR-483/nodel4.html, Feb. 12, 1999.

Smartex, "The Wearable and Wireless Physiological Sensor," 3 pp., http://www.smartex.it/uk/projects/physensor.htm, downloaded on Jun. 4, 2004.

Brown et al., "Agent Supported Information Visualization, Small Unit Operations Communicator", Sep. 25, 2003, Publisher: http://csce/uark.edu/{cwt/DOCS/2003-09--Final-Report--ASIV-SBIR.doc.

Joseph, "Sensors Combat Driver Distraction", "Design News for Mechanical and Design Engineers", Dec. 2, 2002, Publisher: http://www.designnews.com/index.asplayout=articlePrintarticleID=CA260194.

"The AUGCOG Quarterly, Augmented Cognition", Jan. 2004, pp. 5,7, vol. 1, No. 3, Publisher: http://www.atl.external.lmco.com/papers/1193.pdf.

* cited by examiner

COMMUNICATIONS SYSTEM BASED ON REAL-TIME NEUROPHYSIOLOGICAL CHARACTERIZATION

RELATED APPLICATIONS

This application claims the benefit of prior U.S. provisional patent application No. 60/578,812, filed Jun. 9, 2004, which is incorporated herein by reference.

GOVERNMENT LANGUAGE

This invention was made with government support under (DAAD16-03-C-0054) awarded by (Defense Advanced Research Projects Agency through the United States Army Natick Soldier Center). The government has certain rights in this invention.

TECHNICAL FIELD

The present invention relates to communications systems and methods of communication, and more particularly to real time communications systems and methods of communication that use physiological and neurophysiological data for enhanced modes of communication.

BACKGROUND

In contemporary society, individuals are presented with a vast array of information from a myriad of sources. This dense barrage of information taxes individuals, and reduces their understanding of the information that they are presented. New technologies bring yet new forms of information and media, further taxing an individual's ability to interpret and assimilate all of the information. This problem of overburdening individuals with excessive information is especially true in certain professions. For example, modern military forces must operate complicated equipment in taxing environments and stressful situations such as in cockpits, vehicles, aircraft, watch stations and dismounted body-worn systems full of advanced technology. They must work with many devices, interpreting, comparing, relaying, and acting on essential information. However, much of the information that must be sifted through is irrelevant, or is not immediately pertinent. A soldier's efficiency is decreased by the vast quantity of information that he or she must process.

A decrease in efficiency for a soldier can mean the difference between life and death, for himself or his comrades. In situations where information is life-critical, such as in military combat, ensuring a message is received at the right time in the right context is crucial to a combatant's survival. Equally important is delaying the transmission and receipt of non-critical information until life threatening situations have subsided. Even where lives are not on the line, decreased efficiency has a negative impact, drawing a soldier's attention away from currently important tasks. Whether personnel are involved in mission-critical applications, or other non-critical assignments, they must simultaneously process both human and computer-based communications. By decreasing the amount of information that personnel actually receive, and by prioritizing the information that they do receive, their operational performance can be improved. Increased performance will only be provided, however, if they are still presented with immediately pertinent and essential information.

Other professionals, such as police officers, firefighters, emergency first responders, and medical professionals can also benefit from optimizing the presentation of information that they receive. By highlighting the most essential information and reducing the impact of the non-essential information, these professionals can increase their efficiency and improve overall performance and safety.

Therefore there exists a need for an improved communications system.

SUMMARY

The above mentioned problems with real time communications systems and other problems are addressed by embodiments of the present invention and will be understood by reading and studying the following specification.

One embodiment provides a real time communications system. The system includes a communications scheduler adapted to receive one or more messages from a plurality of message sources, a plurality of sensors coupled to the communications scheduler, a display unit, having a plurality of display and control devices, coupled to the communications scheduler, and a database coupled to the communications scheduler. The database includes user specific baseline data. The one or more messages comprise human generated and auto generated messages. The plurality of sensors comprises situational, neurophysiological and physiological sensors. The communications scheduler includes a context manager that receives one or more outputs from the plurality of sensors, monitors a current user's tasks, retains information about the user's environment and receives a current cognitive state profile for the user, a message characterization unit that characterizes the one or more messages using information about the message itself and a presentation unit that receives the characterized messages, the current cognitive state profile, outputs from the plurality of sensors, and the user's specific baseline data to queue the characterized messages into a prioritized message list and presents the message list to the user via the display unit.

Wherein the context manager receives the current cognitive state profile from a cognitive state profile processing unit. Wherein the cognitive state profile processing unit is coupled to the database.

Wherein information about the message itself includes one or more of priority, category, time profile, content, time, response actions, associated tasks, interaction requirements, scheduler feedback, status and source.

One embodiment provides a method of real time communications scheduling. The method includes receiving one or more messages from at least one message source, sensing one or more situational, physiologic, and neurophysiologic parameters for a user, comparing the sensed parameters against one another and determining if any of the sensed parameters are unreliable and determining reliable parameters and comparing the reliable parameters against the user's baseline data and generating a cognitive state profile. The method further includes sending the cognitive state profile to a message presentation unit, generating the user's current contextual data and sending the user's current contextual data information to the message characterization unit and the message presentation unit, characterizing the one or more messages and generating a message characterization profile for each message based on one or more message attributes, the user's current contextual information, and characterization rules and sending the message characterization profiles to a message presentation unit. The method further includes generating a message list according to the user's cognitive state profile, the message characterization profile, the user's current contextual information, and defined message presentation rules and presenting the messages to the user through one or more visual outputs, audio outputs, and tactile outputs based on the message list.

Wherein the reliable parameters are also compared against a set of rules.

DRAWINGS

Figure 1B:
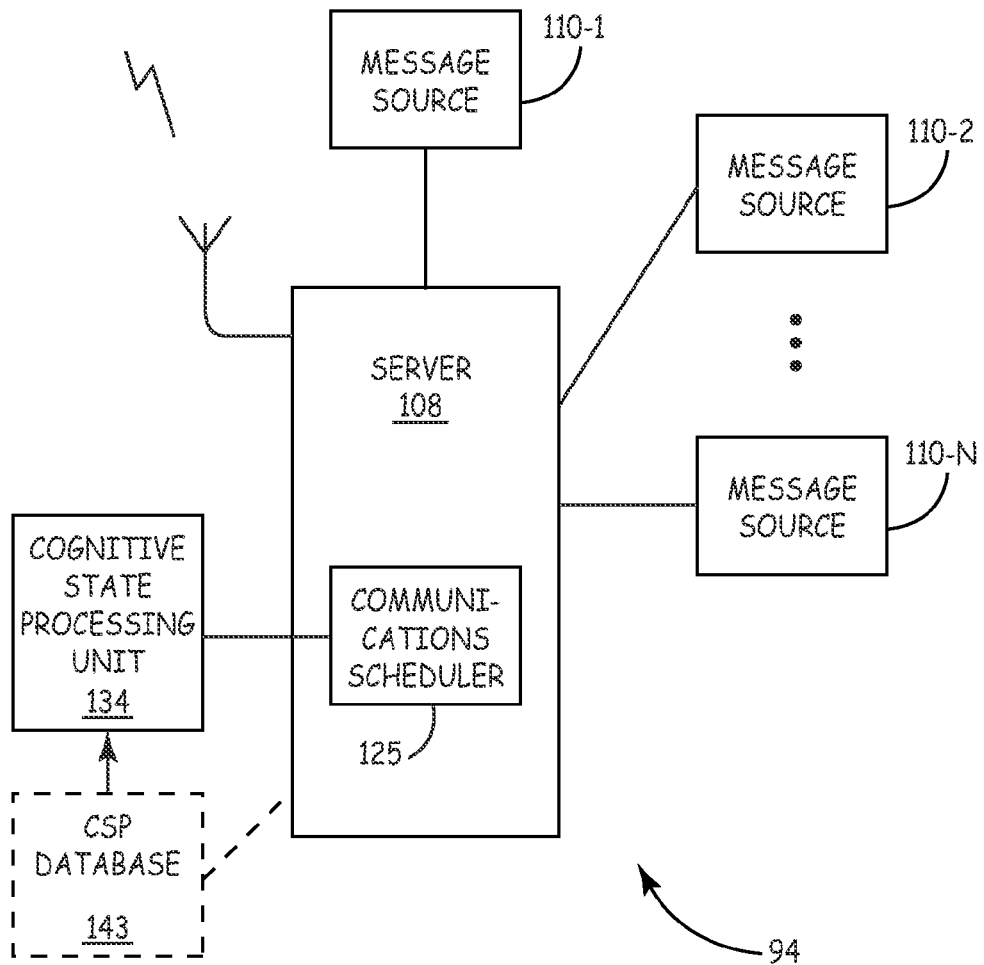
Figure 2:
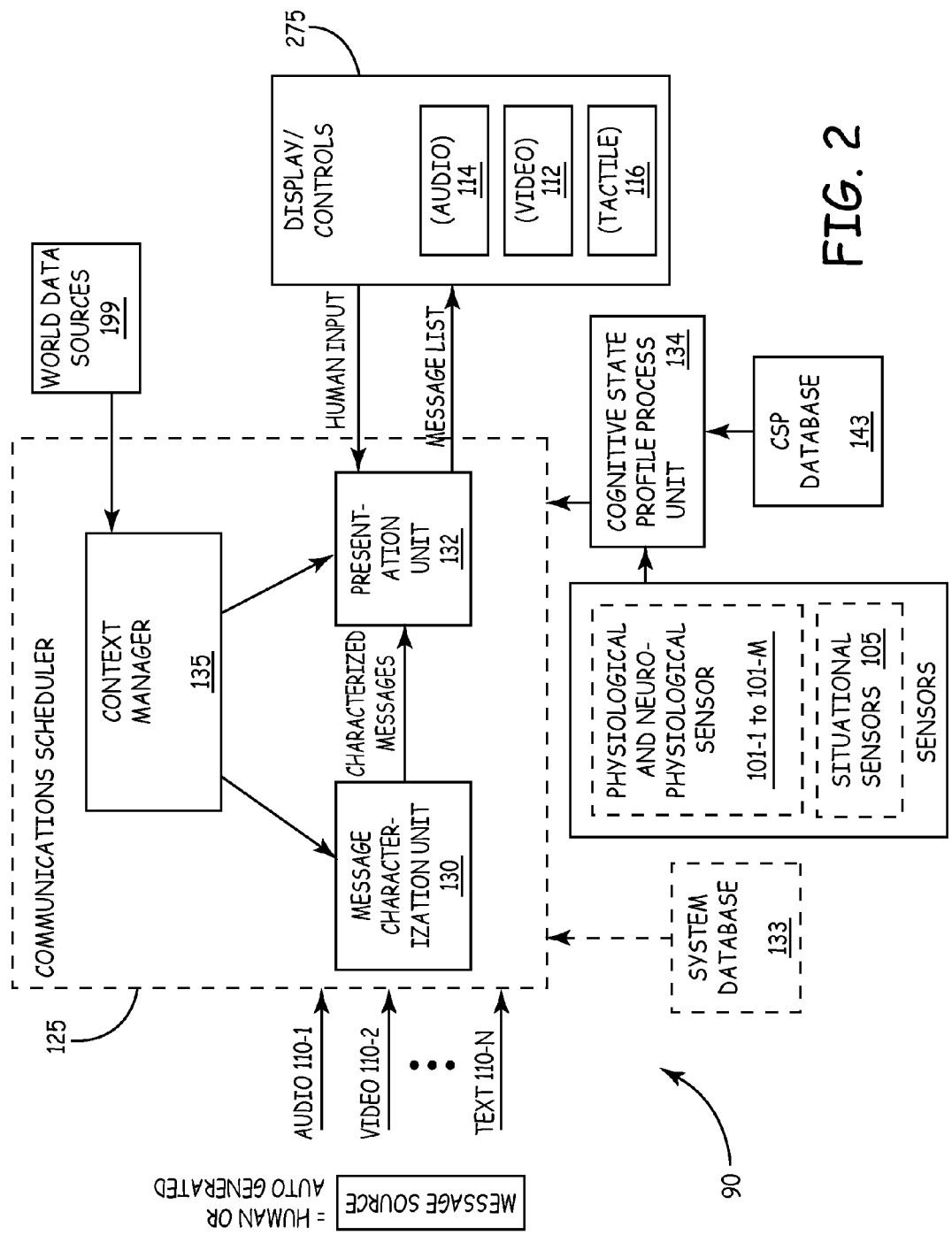
Figure 3:
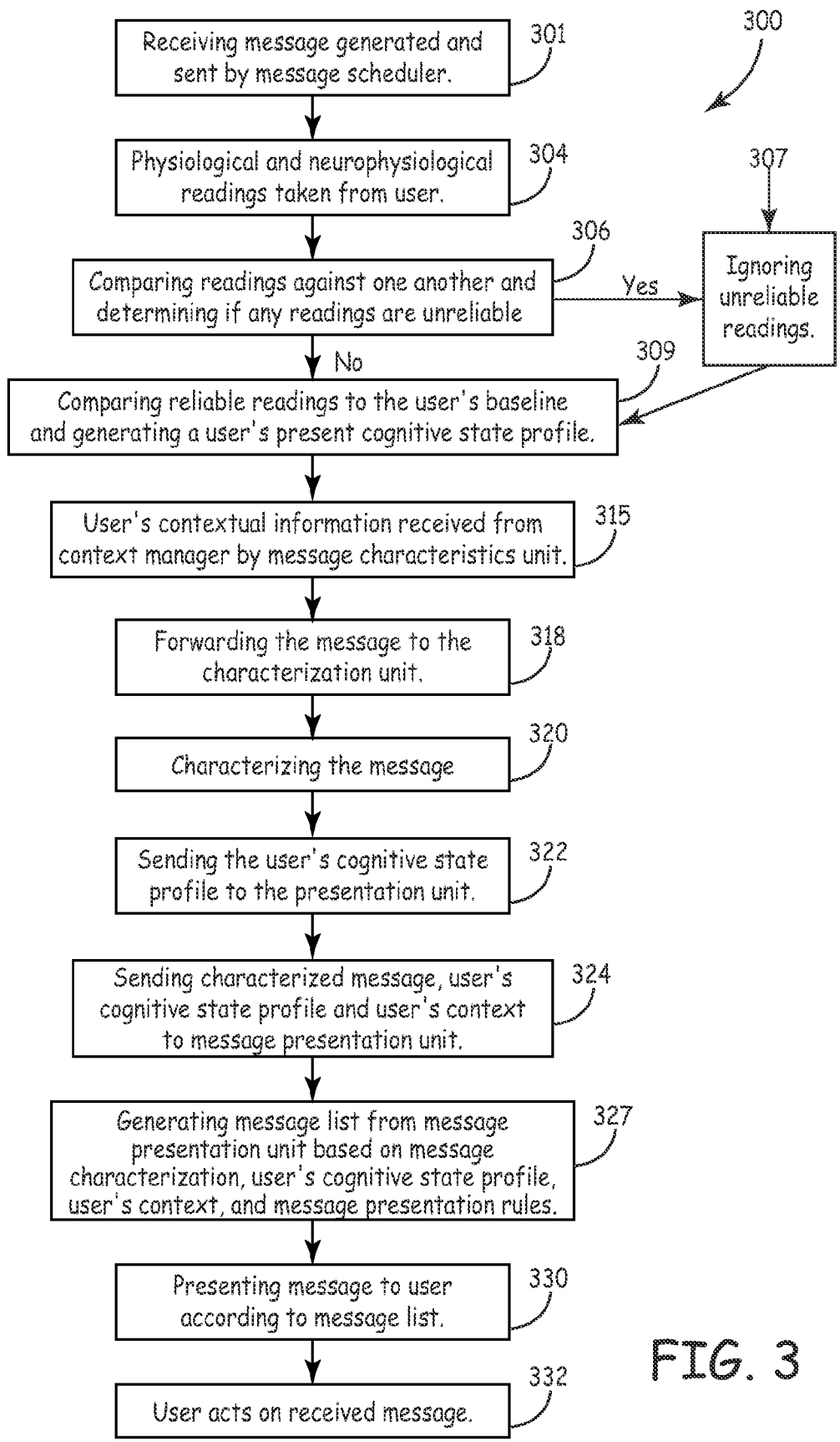

FIG. 1a is one embodiment of a conceptual view of an aspect of a real time communications system in accordance with the present invention, FIG. 1b is one embodiment of a conceptual view of another aspect of a real time communications system in accordance with the present invention, FIG. 2 is one embodiment of a block diagram of a real time communications system in accordance with the present invention, and FIG. 3 is a flow diagram of one embodiment of an implementation of a real time communications system in accordance with the present invention.

DETAILED DESCRIPTION

The primary embodiments of the invention will now be discussed in detail, examples of which are illustrated in the accompanying figures. Illustrated embodiments are presented by way of example and are not to be construed as limitations. All alternatives, modifications, and equivalents that fall within the scope and spirit of the invention are incorporated herein. For example, it is understood by a person of ordinary skill in the art that the present invention can be used both in military and non-military applications. It is further understood that additional physiological and neurophysiological sensors from the ones described herein, though not specifically mentioned, can be used with equal ease and advantage in the present invention.

Embodiments of the present invention may be implemented with present physiological and neurophysiological technologies as well as current computing and telecommunication technologies. This description is presented with enough detail to provide an understanding of the present invention, and should not be construed to encompass all necessary elements in a real time communications scheduling system.

Embodiments of the present invention provide a communications system that is used to mitigate the information processing demands imposed by managing incoming communications. Embodiments of the present invention use information management and modality-appropriate information presentation strategies to direct the user's attention to the highest priority information. Even in situations where there is a continuous flow of verbal and electronic communication, this system is used, for example, to direct a person's attention to the highest priority information source to complete his or her current task or mission within highly dynamic environments. The system uses context modeling, a real-time assessment of a person's cognitive state, and the attributes of the message content to improve overall human-machine system performance through optimal information throughput via communications scheduling. The system is multi-functional, and also has the ability to delay message presentation until a later time for lower priority messages, enhance the highest priority messages, repeat a message if the information was unlikely to have been processed, change the modality if the information is better received through an alternative modality, and the like.

Referring to the drawings, FIGS. 1a and 1b are conceptual views of a real time communications system, based on one embodiment of the present invention. The real time communications system is divided into a user end 92, shown generally in FIG. 1a, and a server end 94, shown generally in FIG. 1b. FIG. 1a depicts a user 99 on whom is arranged a plurality of physiological and neurophysiological sensors 101-1 to 101-M. In one embodiment the plurality of physiological and neurophysiological sensors 101-1 to 101-M include one or more of an electroencephalogram (EEG), electrocardiogram (ECG), electrooculogram (EOG), impedance pneumogram (ZPG), galvanic skin response (GSR) sensor, blood volume pulse (BVP) sensor, respiration sensor, electromyogram (EMG), blood pressure sensor, brain and body temperature sensors, neuro-infrared optical brain imaging sensor, and the like. Physiological and neurophysiological sensors are designed to measure conditions of the mind and body, which in one embodiment are interpreted to characterize the present state of the user 99. In other embodiments, one or more situational sensors 105 are added such as an accelerometer, global positioning system (GPS), or gyroscope. In additional embodiments, the neurophysiological and physiological sensors 101-1 to 101-M and situational sensors 105 are also implemented to define the context or recognize the task in which the user 99 is engaged. In other embodiments, additional measurement devices and sensors are employed to aid in defining the context or recognize the task in which the user 99 is engaged.

Each sensor 101-1 to 101-M is designed to measure a particular aspect of a user's 99 physiology and neurophysiology. In one embodiment, sensors 101-1 to 101-M are used to monitor information on the entire body, examples being respiration, blood flow, brain wave activity, and the like. More specifically, in one embodiment an EEG is used to monitor a user's 99 brain wave activity by sensing electrical potential at the scalp. Measurements by EEG are categorized into frequency bands including delta, theta, alpha, and beta. For example, the delta band, ranging from 1-4 Hz, indicates a state of unconsciousness; the theta band, ranging from 4-8 Hz indicates a state of daydreaming, the alpha band, ranging from 8-13 Hz indicates an alert, but not mentally busy state, and the beta band, ranging from 13-30 Hz indicates a state of higher thought process. Other frequency bands are possible. Based on the EEG site and dominant frequencies detected, EEG data can help detect the type of mental activity. For example, if there are significant brain waves measured in the frontal brain, in one embodiment this indicates that a user 99 is actively manipulating information within their working memory. Therefore the EEG is used to measure the cognitive state of a user 99.

Likewise, the ECG measures heart rate by detecting electrical activity of the heart muscle, the EOG measures eye movement by detecting electrical changes between the front and back of the eye as the eye moves, and the EMG measures currents associated with muscle action. Also, the GSR is measured by sensing changes in conductivity of the skin caused by sweating and saturation of skin ducts prior to sweating, and the BVP measures an individual's heart rate by detecting changes in blood volume at a given location of his or her body.

In one embodiment, more than one physiological and/or neurophysiological measurement can be taken in unison to determine whether a given message should presently be forwarded to a user 99. For example, a user's 99 level of muscle contractions, heart rate, rate of respiration, number and duration of eye blinks, eye movement, and brain activity can together determine if he or she is currently under a situation of stress, or one of ease. In one embodiment, heightened pulse, increased respiration, and rapid muscle contractions indicate that a user 99 is likely not in a position to receive an incoming message that requires concentration since higher level of physiological arousal interferes with the attentional focus required by such complex tasks. Likewise, if an individual has increased levels of theta activity, particularly in the frontal lobe, then he probably is unprepared to attend to an urgent incoming message since high theta activity is indicative of daydreaming or inattention and applying attention getting aspects to the messages are warranted to increase the likelihood of receipt.

Referring back to FIG. 1a, the plurality of physiological and neurophysiological sensors 101-1 to 101-M are electrically connected to a processing unit 103 via a plurality of conductive leads. In one embodiment, the processing unit 103 is in communication with a server 108, of FIG. 1B, through a wireless connection. Server 108 receives messages from a plurality of message sources 110-1 to 110-N. The plurality of message sources comprises messages from human sources and autogenerated messages from the communications scheduler 125 or other systems. Examples of human message sources include audio or text messages from other personnel, commands from superior officers, a broadcast of video surveillance footage, and the like. In one embodiment a communications scheduler 125 processes the messages and determines message priority and whether or not to forward the message to the user 99 through the wireless connection. If the communications scheduler 125 determines to send a message to the user 99, it transmits the message to processing unit 103. Processing unit 103 then outputs the message to the user 99 visually, through a visual output 112, audibly, through an audio output 114, or tactilely, through a tactile output 116. Depending on the priority of the message, the characterization of the message, and the like, one or more outputs can be implemented to relay the message to the user 99. In the illustrated embodiment, communications scheduler 125 is built into server 108. In this embodiment, all or fewer than all of the messages are sent to processing unit 103. In alternative embodiments, communications scheduler 125 is built into the processing unit 103. These embodiments permit all messages to be transmitted to the processing unit 103 before they are sorted and categorized.

In further embodiments, a primary communications scheduler and context manager are built into the server 108, and a backup communications scheduler and context manager are built into the processing unit 103. This embodiment offers the advantage of increased usability at the cost of additional components and/or complication. For example, even if communication is lost between server 108, at the server end 94, and processing unit 103, at the user end 92, message characterization and message presentation continue to update based on changed user 99 status.

In some embodiments, the plurality of physiological and neurophysiological sensors 101-1 to 101-M, processing unit 103, and visual output 112, audio output 114, and tactile output 116 are incorporated into a user's 99 clothing such as a soldier's uniform. For example, in one embodiment the audio and visual output's 112 and 114 and EEG are integrated into the user's 99 head gear such as a helmet, while other physiological and neurophysiological sensors are woven into his clothing. In alternative embodiments, the user end 92 is built into, for example, a vehicle cockpit, a watch station seat, or the like. In some embodiments, all of the user end 92 is incorporated into, for example, the vehicle. In other embodiments only aspects of the user end 92, such as the processing unit 103, are built into the vehicle.

In operation, according to one embodiment, server 108 receives messages from the plurality of message sources 110-1 to 10-N and sends them to the communications scheduler 125. The communications scheduler 125 processes the messages and determines message priority. Physiological and neurophysiological measurements are received from the plurality of physiological and neurophysiological sensors 101-1 to 101-M by the processing unit 103 and forwarded to the presentation unit 132 through cognitive state processing unit 134 at the server end 94. Based on the cognitive state profile and message priority, the presentation unit 132 determines whether to send the message to the processing unit 103 at the user end 92. Messages so designated are sent to the processing unit 103 and presented to the user 99 through one or more of visual outputs 112, audio outputs 114, and tactile outputs 116.

FIG. 2 illustrates a block diagram of a real time communications system, shown generally at 90, in accordance with an embodiment of the present invention. Messages are received by the communications scheduler 125 from a plurality of message sources 110-1 to 110-N and world data sources 199. The received messages can be audio, visual, or textual in nature, or a combination thereof. In one embodiment, the communications scheduler 125 comprises a message characterization unit 130 and a message presentation unit 132. Messages are first processed and characterized by the message characterization unit 130. When characterizing a message, the message characterization unit 130 receives input from a context manager 135. In the illustrated embodiment the context manager 135 is incorporated into the communications scheduler 125. In alternative embodiments, the context manager 135 is separate from the communications scheduler 125.

The context manager 135 monitors the current mission or activity status of the user 99. For example, for military personnel, the context manager 135 keeps track of such information as whether the user 99 is in combat, who the other personnel in his unit are, and who his commanding officer is. In one embodiment, context manager 135 receives data from one or more external sources (world data sources) 199. In one embodiment, the world data sources include one or more of environmental sensor data such as chemical sensors, weather sensors, mission type and the like. Context manager 135 also retains information, for example, on a user's 99 environment, surroundings, and character of present task. Information from the plurality of physiological and neurophysiological sensors 101-1 to 101-M also aids in the characterization of messages. For example, in one embodiment if the plurality of sensors show that user 99 is unconscious or dead, then all messages to the user 99 are characterized as obsolete. In other embodiments, under certain conditions, such as the death of the user 99, messages can be passed on to another user.

Messages are organized by a plurality of message attributes. In one embodiment, messages are organized, for example, by priority, category, time profile, content, time, response actions, associated tasks, interaction requirements, scheduler feedback, status, and source. Priority is subdivided into the classes of high, medium, and low; high priority being assigned to messages that are both mission and time critical, medium priority being assigned to messages that are mission critical, and low priority being assigned to messages that are non-critical. In one embodiment, another class of priority is defined for irrelevant messages for purposefully blocked data. Category comprises the message type, such as reports, commands, status updates, information, and coordination (for example, between units within a single mission). In one embodiment, the time profile comprises response time, time type, duration, and any deadlines. Response time can vary from none, to uncertain, to a certain preset response time. Time type comprises constant, sporadic, and scheduled. Duration comprises the stop time, start time, and any designated period. Deadlines vary, for example, from requiring that a command sent by the message be executed by a particular time, or not before a particular time, or within a set time frame.

Response actions by the user 99 comprise acknowledging, forwarding, deferring, deleting, and ignoring the message, and the like. Further the user 99 can create and send messages to other humans back to the communications system and the like. The communications system 90 is fully interactive with the user 99. Associated tasks and interaction requirements are any of a myriad of tasks and requirements that are attached to a message. These parameters are varied, and may be individualized to particular messages or messages associated with a particular mission or assignment. Scheduler feedback is automated feedback from the real time communications system 90 to the user 99 that indicates to the user 99 that the scheduler has done something to a message. For example, a scheduler feedback message might be one that informs the user 99 that a message has been deferred.

In alternative embodiments, scheduler feedback also comprises automated messages generated by communications scheduler 125. For example, in one embodiment when measurements of a user's 99 present GSR and breath moisture indicate that a user is becoming dehydrated, then an automated message is sent both to the user 99 and the user's commanding officer notifying them that the user is approaching dehydration. In this manner a commanding officer or medic can better monitor the health of his unit. In certain embodiments, automated messages are also generated, for example, to notify members of a unit when comrades are under attack or perished. A message's status comprises such states as pending, deleted, current, expired, acknowledged, deferred, and the like. The source contains information such as the identity of the sender, where the message is being sent from, and when the message was sent.

In one embodiment, the message characterization unit 130 applies user-defined criteria when determining a message's characterization profile. For example, a platoon leader in a military setting might indicate to the system that all communications from squad leaders and the company commander are high priority. He could further indicate that messages from other individuals, such as other platoon leaders, are high priority when the message content includes information about his current task. Additionally, the user 99 could set the communications scheduler such that, for example, if his engagement level, as indicated by a derived EEG measure form select sites and frequencies, is high, then medium and low priority messages not related to his current task are to be deferred. In one embodiment, message priority is set in the message characterization unit 130.

The message characterization unit 130 assigns a characterization profile to each message based on a compilation of the message attributes, thereby characterizing the message. Characterized messages are then sent to the presentation unit 132. The presentation unit 132 receives the characterized message, as well as information from the context manager 135 and the plurality of physiological and neurophysiological sensors 101-1 to 101-M through the cognitive state profile processing unit 134. Data is compiled from the plurality of physiological and neurophysiological sensors 101-1 to 101-M to form a cognitive state profile on the user 99. The cognitive state profile is a real time assessment of the user's 99 present mental and physical state based on the sensor readings. In one embodiment, a cognitive state profile database 143 is coupled to cognitive state profile processing unit 134 and includes a trained set of data that baselines the neurophysiological and physiological state for individual users.

In one embodiment, the cognitive state profile assesses the user's 99 present task engagement, cognitive workload, physiological arousal, novelty level, executive load index, and stress level. Novelty level and executive load index are derived gauges that comprise combinations or processed inputs both from an EEG that indicate the user's 99 attentional state. In one embodiment, the novelty level, executive load index, and the like, are used to assess the likelihood that an incoming message was processed. To accurately determine a user's 99 present task engagement, cognitive workload, and physiological arousal, novelty level, executive load index, and stress level a baseline profile is established for each individual.

In one embodiment, the baseline profile is established through the use of cognitive state classifier via neural networks. A neural network is a form of multiprocessor computer system comprising: simple processing elements, a high degree of interconnection, simple scalar messages, and an adaptive interaction between the elements. The advantage of a neural network is that it can adapt based on new input. In one embodiment, a neural network is used to train the real time communications system 90 to recognize the physiological and neurophysiological readings that correspond to what physical and mental state for each individual. This is done by training individuals in different situations and determining a range of sensor readings for each situation. For example, a user would be trained under a situation of high cognitive stress, and thereafter the real time communications system 90 uses the baseline profile data to accurately tell when the individual is in a situation of high cognitive stress. It is important that a baseline profile be established for each individual in a myriad of different situations, since body responses vary widely between different persons. In one embodiment, a system database 133 is coupled to communications scheduler 125 and includes user preferences, message priorities, task tracking information and other system data.

In one embodiment, baseline profile information for all users is stored at the server end 94 in a cognitive state processing database 143. In alternative embodiments, a user's baseline profile information is stored at the user end 92 in a database such as database 143 attached to his processing unit 103. In further embodiments baseline profile information for all users is stored in a cognitive state processing database 143 attached to each processing unit 103. In conjunction with these embodiments, backup information of each user's 99 baseline profile is stored in a cognitive state processing database 143 that acts as a backup unit.

Under certain situations, some measurements from the physiological and neurophysiological sensors become inaccurate. In applying presentation rules, the message presentation unit 132 qualifies the measurements by using, for example, measurements from an accelerometer to determine if the proper indicia are present such that a particular measurement is presently unreliable. In one embodiment, when situational sensors 105 such as an accelerometer or physiological sensors such as an EMG located around the user's legs indicate high user 99 activity, output from one or more neurophysiological sensor are considered unreliable. For example, when a user 99 is under a high degree of physical activity, as measured for example by accelerometer and EMG, EEG signal quality is more suspect. Therefore, before applying the user's 99 EEG-based profiling to the presentation rules, the message presentation unit 132 first determines whether the EEG readings are reliable. Other examples wherein one or more sensor readings are implemented to qualify another sensor reading include: comparing the BVP, ECG, and respiration sensors against one another, or comparing the GSR, EMG, and ECG against each other. In the first example, both the BVP and ECG measure heart rate, but by different means, while the respiration sensor measures breath rate. In this example, if the BVP and ECG both output different readings, then they are checked against the user's breath rate. Since a high breath rate generally accompanies an increased pulse, the breath rate can be used to determine which of the heart rate monitors is more accurate. Additionally, for the second example an increased GSR reading is generally accompanied by an increased EMG and ECG reading. Therefore if any two of the GSR, EMG, and ECG are significantly different from the third sensor, then that third sensor is suspect. Suspect sensor readings may indicate false readings due to, for example, a failing sensor or poor contact between the sensor and user 99. In one embodiment, for example, when readings from an accelerometer indicate that the user 99 is under a moderate to high degree of acceleration, EEG readings are marked as unreliable. In some embodiments, when the readings of a particular sensor are presently unreliable, those readings might be ignored for the generation of the user's 99 current cognitive state profile.

Based on the user's 99 present context, his cognitive state profile, and the characterization profile attached to a message or messages, the message or messages are queued into a message list. Messages are then presented to the user 99 based on the message list. In one embodiment, the message list is continually updated on a real time basis. A continually updated message list eliminates presenting unnecessary or obsolete messages to the user 99, and ensures that the most important messages will be received before less important ones.

The message presentation unit 132 takes actions and prepares the message list based on a list of actions that comprises the commands of: pass through, delete, defer, reschedule, divert attention to message, escalate, and change modality, and the like. The pass through action indicates that the message remains unchanged by the scheduler. The change modality action changes or adjusts a message's presentation format. For example in certain embodiments a change modality action changes in the presentation mode from visual to aural. Actions that are assigned to a message occur in addition to or instead of assigning the message to the message list. For example, to divert attention to high priority messages, an alert may sound immediately prior to the presentation of that high priority message. When the escalate command is attached to a message, the alert tone normally presented before a high priority message will be made salient and more attention-grabbing, in order to escalate the system's ability to direct user 99's attention towards the incoming message.

Additionally, the message presentation unit 132 assigns a mode or modes of presentation for each message. In one example, a message is presented to the user 99 through one or more audio, visual, and tactile communication methods, shown collectively as 275, and individually as audio output 114, visual output 112, and tactile output 116. Depending on the urgency and nature of the message, and other factors in the characterization profile, the message presentation unit 132 assigns one or more communication methods. For example, a single message might be presented with an audio, visual, and tactile aspect. A single communication method can also have multiple forms of presentation. For example, in one embodiment both light emitting diodes and a video display are used to present visual data to the user 99.

Rules of presentation are more rigid than rules of characterization. In one embodiment all the possible responses and actions to be carried out are preprogrammed into the message presentation unit 132. Therefore, in one embodiment, once the message has been characterized, the presentation unit applies its rules to the message and acts accordingly.

In one embodiment the communications scheduler 125, and therefore the message characterization unit 130 and message presentation unit 132, is hard wired into the server 108 or processing unit 103. In other embodiments the communications scheduler 125 comprises software and is programmed into the server 108 or processing unit 103. In alternative embodiments, the message characterization unit 130 and message presentation unit 132 are separate functions of a single unit. For example, the message characterization unit 130 and message presentation unit 132 are different modes of one software implementation.

Messages are presented to the user 99 in accordance with the message list. After being alerted of a message's presence, a user 99 takes one or more actions, from a list comprising: forwarding the message, acknowledging the message, deleting the message, responding to the message, ignoring the message, and the like. The user's 99 action is sent to the real time communications system 90, which then updates the messages characterization profile based on the action.

FIG. 3 shows a flow diagram depicting one example of an implementation of a real time communications system 90 in accordance with one embodiment. The illustrated implementation of the real time communications system 90 begins with the step of receiving a message that has been generated and sent to the communications scheduler 301. In step 304, physiological and neurophysiological readings are taken from the user. Step 306 comprises comparing readings against one another to determine if any readings are unreliable. In one embodiment readings from situational sensors are compared against physiological and neurophysiological readings. When situational sensors indicate a high level of user activity, output from neurological sensors is considered less reliable. When unreliable readings are indicated, those unreliable readings may be ignored 307. Reliable readings are compared to a baseline profile to generate a user's present cognitive state profile, step 309. A user's contextual information is received from the context manager 135 by a message characterization unit in step 315. Step 318 comprises forwarding the message to the message characterization unit. Then the method proceeds to 320, and the message is characterized by the message characterization unit based on message attributes, the user's context, and message characterization rules. In step 322, the user's cognitive state profile is sent to the presentation unit. In step 324 the characterized message is sent to the message presentation unit, to be influenced by the user's cognitive state profile and context. A message list is generated by the message presentation unit based on message characterization, the user's cognitive state profile, the user's context, and message presentation rules in step 327. In step 330, the message is displayed to the user according to the message list. Finally, in step 332 the user takes any applicable actions in response to the message.

In view of the foregoing, it will be understood by those skilled in the art that the methods of the present invention can be implemented in combination with present computing and communications technology. Variations and modifications may occur, which fall within the scope of the present invention, as set forth in the following claims.

What is claimed is:

1. A communications system, comprising:
   a communications scheduler adapted to receive one or more messages from a plurality of message sources, wherein the one or more messages comprise human generated and auto generated messages;
   a plurality of sensors coupled to the communications scheduler, wherein the plurality of sensors comprise situational, neurophysiological and physiological sensors; and
   a display unit, having a plurality of display and control devices, coupled to the communications scheduler;
   wherein the communications scheduler includes:
      a context manager that receives one or more outputs from the plurality of sensors, monitors a current user's tasks, and retains information about the user's environment;
      a message characterization unit that characterizes the one or more messages using message attributes, outputs from the plurality of sensors, and the current user's specific baseline profile data; and
      a presentation unit that receives the characterized messages, queues the characterized messages into a prioritized message list and presents the message list to the user via the display unit.

2. The system of claim 1, further comprising a cognitive state profile processing unit that generates a cognitive state profile for the current user.

3. The system of claim 2, further comprising a cognitive state profile database coupled to the communications scheduler, wherein the database includes current user specific baseline profile data.

4. The system of claim 3, wherein the cognitive state profile processing unit receives output from the plurality of sensors and the current user's specific baseline profile data in order to generate the cognitive state profile.

5. The system of claim 1, wherein the context manager further receives one or more data feeds from external sources.

6. The system of claim 5, wherein the one or more data feeds include one or more of chemical sensors, weather sensors, and mission data.

7. The system of claim 2, wherein the context manager receives the current cognitive state profile from the cognitive state profile processing unit.

8. The system of claim 1, wherein the message attributes include one or more of priority, category, time profile, content, time, response actions, associated tasks, interaction requirements, scheduler feedback, status and source.

9. The system of claim 1, wherein the one or more messages comprise audio, video and text messages.

10. The system of claim 2, wherein the presentation unit uses the characterized messages, the current cognitive state profile and message presentation rules to continually optimize the characterized messages for presentation to the user.

11. The system of claim 1, wherein the plurality of display devices present the prioritized message via one or more audio, video, and tactile devices.

12. The system of claim 1, wherein the human generated and auto generated messages comprise text messages, audio messages, video messages and tactile messages.

13. The system of claim 1, wherein the physiological sensors comprise one or more of an ECG, EOG, ZPG, GSR, BVP, respiration sensor, EMG, blood pressure sensor, brain and body temperature sensors, and near-infrared optical brain imaging sensor.

14. The system of claim 1, wherein the situational sensors comprise one or more of an accelerometer, gyroscope and global positioning system receiver.

15. The system of claim 1, wherein the situational sensors comprise one or more of neurophysiological and physiological sensors.

16. The system of claim 2, wherein the cognitive state profile comprises assessments of one or more of the user's present task engagement, cognitive workload, stress level, and physiological arousal.

17. A method of communications scheduling comprising:
   receiving one or more messages from at least one message source;
   sensing one or more situational, physiological, and neurophysiological parameters associated with a user;
   comparing the sensed parameters against one another;
   determining if any of the sensed parameters are unreliable;
   determining one or more reliable parameters;
   comparing the reliable parameters against baseline profile data for the user;
   generating a cognitive state profile based on the reliable parameters and the user's baseline profile data;
   sending the cognitive state profile to a message presentation unit;
   generating the user's current contextual data and sending the user's current contextual data information to the message characterization unit;
   characterizing the one or more messages and generating a message characterization profile for each message based on one or more message attributes, the user's current contextual information, and characterization rules;
   sending the message characterization profiles to a message presentation unit;
   generating a message list according to the user's cognitive state profile, the message characterization profile, the user's current contextual information, and defined message presentation rules; and
   presenting the messages to the user through one or more visual outputs, audio outputs, and tactile outputs based on the message list.

18. The method of claim 17, wherein the one or more messages comprise one or more human generated messages and auto-generated messages.

19. The method of claim 17, wherein the one or more situational, physiological and neurophysiological parameters comprise at least one of an EEG measurement, an ECG measurement, an EOG measurement, a ZPG measurement, GSR, BVP, respiration, an EMG measurement, blood pressure, brain and body temperature, acceleration, and location.

20. The method of claim 17, wherein generating the message list comprises queuing messages into the message list based on the user's cognitive state profile, the user's contextual information, the message characterization profile, and rules of presentation.

21. A communications system, comprising:
   a means for receiving one or messages from at least one message source;
   a means for sensing a plurality of situational, physiological, and neurophysiological parameters associated with a user;
   a means for comparing the sensed parameters against one another and determining if any of the sensed parameters are unreliable;
   a means for determining one or more reliable parameters;
   a means for comparing the reliable parameters against the user's baseline profile data;

a means for generating a cognitive state profile based on the reliable parameters and the user's baseline profile data;

a means for sending the cognitive state profile to a message presentation unit;

a means for generating the user's current contextual data and sending the user's current contextual data information to the message characterization unit;

a means for characterizing the one or more messages and generating a message characterization profile for each message based on one or more message attributes, the user's current contextual information, and characterization rules;

a means for sending the message characterization profiles to a message presentation unit;

a means for generating a message list according to the user's cognitive state profile, the message characterization profile, the user's current contextual information, and defined message presentation rules; and a means for presenting the messages to the user through one or more visual outputs, audio outputs, and tactile outputs based on the message list.

22. The system of claim 21, wherein the one or more messages comprise one or more human generated messages and auto-generated messages.

23. The method of claim 21, wherein the one or more situational, physiological and neurophysiological parameters comprise at least one of an EEG measurement, an ECG measurement, an EOG measurement, a ZPG measurement, GSR, BVP, respiration, an EMG measurement, blood pressure, brain and body temperature, acceleration, and location.

24. The system of claim 21, wherein the means for generating the message list comprises a means for queuing messages into the message list based on the user's cognitive state profile, the user's contextual information, the message characterization profile, and rules of presentation.

25. A communications system, comprising:

a plurality of sensors comprising situational, neurophysiological and physiological sensors;

processing functionality coupled to the plurality of sensors and configured to:

receive output from the plurality of sensors;

receive a database that includes the current user's specific baseline data;

receive a user's specific baseline data;

generate a cognitive state profile based on the output and the user's specific baseline data;

receive one or more messages, wherein each message has attributes; and characterize the one or more messages based on at least the message attributes of the messages and the cognitive state profile of the user.

26. The system of claim 25, wherein the processing functionality comprises a communications scheduler adapted to receive the one or more messages, and wherein the communication scheduler includes a context manager that receives the sensor output from the plurality of sensors and receives one or more data feeds from external sources.

27. The system of claim 26, wherein the one or more data feeds include one or more of chemical sensors, weather sensors, and mission data.

28. The system of claim 26, wherein the processing functionality comprises a cognitive state profile processing unit that generates the cognitive state profile, and wherein the context manager receives the cognitive state profile from the cognitive state profile processing unit.

29. The system of claim 25, wherein the message attributes include one or more of priority, category, time profile, content, time, response actions, associated tasks, interaction requirements, scheduler feedback, status and source.

30. The system of claim 25, wherein the one or more messages comprise audio, video and text messages.

31. The system of claim 25, wherein the processing functionality further comprises a presentation unit that receives the characterized messages, queues the characterized messages into a prioritized message list and presents the message list to the user via a display unit, and wherein the presentation unit uses the characterized messages, the current cognitive state profile and message presentation rules to continually optimize the characterized messages for presentation to the user.

32. The system of claim 25, wherein the one or more messages comprise text messages, audio messages, video messages and tactile messages.

33. The system of claim 25, wherein the physiological sensors comprise one or more of an ECG, EOG, ZPG, GSR, BVP, respiration sensor, EMG, blood pressure sensor, brain and body temperature sensors, and near-infrared optical brain imaging sensor.

34. The system of claim 25, wherein the situational sensors comprise one or more of an accelerometer, gyroscope and global positioning system receiver.

35. The system of claim 25, wherein the situational sensors comprise measures derived from one or more of neurophysiological and physiological sensors.

36. The system of claim 25, wherein the cognitive state profile comprises assessments of one or more of the user's present task engagement, cognitive workload, stress level, and physiological arousal.

* * * * *